US012747426B1

(12) United States Patent
Covalin et al.

(10) Patent No.: US 12,747,426 B1
(45) Date of Patent: Sep. 29, 2026

(54) EX-VIVO ENHANCEMENT OF PLATELET FUNCTION DURING BLOOD PROCESSING

(71) Applicant: Spark Biomedical, Inc., Dallas, TX (US)

(72) Inventors: Alejandro Covalin, Los Angeles, CA (US); Navid Khodaparast, Dallas, TX (US)

(73) Assignee: Spark Biomedical, Inc., Dallas, TX (US)

( * ) Notice: Subject to any disclaimer, the term of this patent is extended or adjusted under 35 U.S.C. 154(b) by 0 days.

(21) Appl. No.: 19/373,244

(22) Filed: Oct. 29, 2025

(51) Int. Cl.
*C12N 5/00* (2006.01)
*A61M 1/38* (2006.01)

(52) U.S. Cl.
CPC ............. *C12N 5/526* (2025.01); *C12N 5/562* (2025.01); *A61M 1/382* (2013.01); *A61M 2202/0427* (2013.01)

(58) Field of Classification Search
CPC ................... C12N 5/526; C12N 5/562; A61M 2202/0427; A61M 37/00
See application file for complete search history.

(56) References Cited

U.S. PATENT DOCUMENTS

| | | | | |
|---|---|---|---|---|
| 5,314,826 | A | 5/1994 | Baugh | |
| 6,735,476 | B2 | 5/2004 | Mellen | |
| 7,657,310 | B2 | 2/2010 | Buras | |
| 7,711,432 | B2 | 5/2010 | Thimineur et al. | |
| 8,562,658 | B2 | 10/2013 | Shoham et al. | |
| 8,729,129 | B2 | 5/2014 | Tracey et al. | |
| 8,914,123 | B2 | 12/2014 | Rigaux | |
| 8,942,814 | B2 | 1/2015 | Szeles | |
| 9,089,719 | B2 | 7/2015 | Simon et al. | |
| 9,925,373 | B2 | 3/2018 | Nirenberg | |
| 10,207,106 | B2 | 2/2019 | Simon et al. | |
| 10,463,854 | B2 | 11/2019 | Perez | |
| 10,537,703 | B2 | 1/2020 | Tyler et al. | |
| 10,750,739 | B2 | 8/2020 | Sandlin et al. | |
| 10,786,666 | B2 | 9/2020 | Chu et al. | |
| 10,912,712 | B2 | 2/2021 | Tracey et al. | |
| 10,967,182 | B2 | 4/2021 | Khodaparast et al. | |
| 11,260,229 | B2 | 3/2022 | Manogue | |
| 11,351,370 | B2 | 6/2022 | Covalin et al. | |
| 11,660,443 | B2 | 5/2023 | Huston et al. | |
| 12,029,733 | B2 | 7/2024 | Bright et al. | |
| 12,390,640 | B2 | 8/2025 | Covalin et al. | |
| 2005/0065574 | A1 | 3/2005 | Rezai | |
| 2009/0287035 | A1 | 11/2009 | Dietrich et al. | |
| 2011/0076669 | A1 * | 3/2011 | Sehgal | A01N 1/02 435/2 |
| 2011/0190668 | A1 | 8/2011 | Mishelevich | |
| 2014/0135886 | A1 | 5/2014 | Cook et al. | |
| 2014/0206945 | A1 | 7/2014 | Liao | |
| 2015/0335876 | A1 | 11/2015 | Jeffery et al. | |
| 2018/0200522 | A1 | 7/2018 | Taca, Jr. | |
| 2019/0134390 | A1 | 5/2019 | Shimada et al. | |
| 2019/0321623 | A1 | 10/2019 | Huston et al. | |
| 2020/0086124 | A1 | 3/2020 | Kibler et al. | |
| 2020/0094055 | A1 | 3/2020 | Manogue | |
| 2020/0238085 | A1 | 7/2020 | Khodaparast et al. | |
| 2021/0213286 | A1 | 7/2021 | Covalin et al. | |
| 2022/0192580 | A1 | 6/2022 | Toth et al. | |
| 2022/0212012 | A1 | 7/2022 | Manogue | |
| 2022/0305260 | A1 | 9/2022 | Covalin et al. | |
| 2024/0042201 | A1 | 2/2024 | Huston et al. | |
| 2024/0285944 | A1 * | 8/2024 | Covalin et al. | A61N 1/36 |
| 2024/0399145 | A1 | 12/2024 | Covalin et al. | |
| 2025/0041598 | A1 | 2/2025 | Covalin et al. | |

FOREIGN PATENT DOCUMENTS

| | | | |
|---|---|---|---|
| RU | 2239408 | C2 | 11/2004 |
| WO | WO1998016548 | A1 | 4/1998 |
| WO | WO2021011165 | A1 | 1/2021 |
| WO | WO2024178132 | A2 | 8/2024 |

OTHER PUBLICATIONS

Bennett et al. (2019) "Acetylcholine inhibits platelet activation" The Journal of pharmacology and experimental therapeutics, 369(2), 182-187. (Year: 2019).*

Van der Meer et al. (2011) "Platelet preservation: agitation and containers" Transfusion and apheresis Science, 44(3), 297-304. (Year: 2011).*

Meng et al. (2022) "The alpha-7 nicotinic acetylcholine receptor agonist GTS-21 engages the glucagon-like peptide-1 incretin hormone axis to lower levels of blood glucose in db/db mice" Diabetes Obes Metab., 24(7):1255-1266, Author manuscript, PMID: 35293666, PMCID: PMC9177741. (Year: 2022).*

Abbasian, et al., "Supramaximal Calcium Signaling Triggers Procoagulant Platelet Formation", Blood Advances, Dept. of Pharmacology and Dept. of Biochemistry, Universit of Cambridge, Cambridge, UK, Jan. 2020, vol. 4, No. 1, pp. 154-164.

Ali, Soleimany Ferizhandy, "Platelet Activation in Stored Platelet Concentrates: Comparison of Two Methods Preparation," J Hematol (2012), vol. 1(1). pp. 15-19.

Bennett, et al. "Acetylcholine Inhibits Platelet Activation", The Journal of Pharmacology and Experimental Therapeutics, May 2019, pp. 182-187.

(Continued)

*Primary Examiner* — James Joseph Graber

(74) *Attorney, Agent, or Firm* — Secant IP, PLLC

(57) ABSTRACT

In an illustrative embodiment, enhancing platelet function ex-vivo includes treating blood (e.g., whole blood or separated platelets) extracted from a subject with calcium ions and one or more reagents, each reagent configured to activate at least one transmembrane Ca2+ channel, such that the combined calcium ions and reagent(s) cause a portion of platelets within the blood to undergo enhancement via activation of the transmembrane Ca2+ channel(s), thereby producing a population of enhanced platelets within the blood having increased Ca2+ for enhanced coagulation capability. The blood may be returned to the subject or stored for later use.

25 Claims, 6 Drawing Sheets

(56) References Cited

OTHER PUBLICATIONS

Bitner, et al., "In Vivo Pharmacological Characterization of a Novel Selective d7 Neuronal Nicotinic Acetylcholine Receptor Agonist ABT-107: Preclinical Considerations in Alzheimer's Disease," The Journal of Pharmacology and Experimental Therapeutics, (2010), vol. 334, No. 3. pp. 875-886.
Bodnar, et al., "Discovery and Structure-Activity Relationship of Quinuclidine Benzamides as Agonists of α7 Nicotinic Acetylcholine Receptors," J. Med. Chem. (2005), vol. 48, pp. 905-908.
Bravo-Iniguez, Carlos E., et al., "Vagus nerve stimulation primes platelets and reduces bleeding in hemophilia A male mice", Nature Communications, Jun. 2023, 12 pages.
Briggs, et al., "Functional Characterization of the Novel Neuronal Nicotinic Acetylcholine Receptor Ligand GTS-21 in Vitro and In Vivo," Pharmacology Biochemistry and Behavior, (1997), vol. 57, Nos. 1/2, pp. 231-241.
Di Ciano, et al., "The GABAb Receptor Agonist Baclofen Attenuates Cocaine and Heroin-Seeking Behavior by Rats," Neuropsychopharmacology (2003), vol. 28, pp. 510-518.
Dobryakova, et al., "The Dopamine Imbalance Hypothesis of Fatigue in Multiple Sclerosis and Other Neurological Disorders", Frontiers in Neurology, Mar. 2015, vol. 6, Article 52, pp. 1-8.
Elboim-Gabyzon, et al., "Transcutaneous Electrical Nerve Stimulation (TENS) for Primar Dysmenorrhea: An Overview", International Journal of Women's Health, Dovepress, (2020), vol. 12, pp. 1-10.
Azuma, et al., "Metabolism and disposition of GTS-21, a novel drug for Alzheimer's disease," Xenobiotica,(1999), vol. 29, No. 7. pp. 747-762.
Freedman, et al., "Initial Phase 2 Trial of a Nicotinic Agonist in Schizophrenia," Am J Psychiatry (2008), vol. 165. pp. 1040-1047.
Hajós, et al., "The Selective d7 Nicotinic Acetylcholine Receptor Agonist PNU-282987 [N-[(3R)-1-Azabicyclo[2.2.2]oct-3-yl]-4-chlorobenzamide Hydrochloride] Enhances GABAergic Synaptic Activity in Brain Slices and Restores Auditory Gating Deficits in Anesthetized Rats," The Journal of Pharmacology and Experimental Therapeutics, (2005), vol. 312, No. 3. pp. 1213-122.
Kem, et al., "Hydroxy Metabolites of the Alzheimer's Drug Candidate 3-[(2,4-Dimethoxy)Benzylidene]-Anabaseine Dihydrochloride (GTS-21): Their Molecular Properties, Interactions with Brain Nicotinic Receptors, and Brain Penetration," Molecular Pharmacology (2004), vol. 65, No. 1. pp. 56-67.
Kem, et al., "Pharmacokinetic Limitations on Effects of an Alpha7-Nicotinic Receptor Agonist in Schizophrenia: Randomized Trial with an Extended-Release Formulation," Neuropsychopharmacology (2018), vol. 43. pp. 583-589.
Kitagawa, et al., "Safety, Pharmacokinetics, and Effects on Cognitive Function of Multiple Doses of GTS-21 in Healthy, Male Volunteers," Neuropsychopharmacology (2003), vol. 28. pp. 542-551.
Lei, Kin Fong, et al. "Real-time electrical impedimetric monitoring of blood coagulation process under temperature and hematocrit variations conducted in a microfluidic chip." PLoS One Oct. 2013, vol. 8.10, 7 pages.
Mahnir, et al., "Pharmacokinetics and Urinary Excretion of DMXBA (GTS-21), a Compound Enhancing Cognition," Biopharmaceutics & Drug Disposition, (1998), vol. 19. pp. 47-151.
Kooijman, et al., "Hematopoietic d 7 nicotinic acetylcholine receptor deficiency increases inflammation and platelet activation status, butdoes not aggravate atherosclerosis," Journal of Thrombosis and Haemostasis, (2015), vol. 13, pp. 126-135.
Malysz, et al., "In Vitro Pharmacological Characterization of a Novel Selective d7 Neuronal Nicotinic Acetylcholine Receptor Agonist ABT-107," The Journal of Pharmacology and Experimental Therapeutics (2010), vol. 334, No. 3. pp. 863-874.
Martinez-Perèz, et al. "Continuous detection of increasing concentrations of thrombin employing a label-free photonic crystal aptasensor." Micromachines 11.5 (2020): 12 pages.
McLagan et al., "The Role of Transcutaneous Electrical Nerve Stimulation for Menstrual Pain Relief: A Randomized Control Trial", Women's Health, (2024), vol. 20, pp. 1-10.
Nettle, "A New Care Pathway for Menstrual Health", http://www.samphireneuro.com/nettle/health-care-providers, accessed Nov. 5, 2024, 16 pages.
Olincy, et al., "Proof-of-Concept Trial of an 7 Nicotinic Agonist in Schizophrenia," Arch Gen Psychiatry, (2006), vol. 63. pp. 630-638.
Radek, et al., "Effects of the Novel σ7 Nicotinic Acetylcholine Receptor Agonist ABT-107 on Sensory Gating in DBA/2 Mice: Pharmacodynamic Characterization," The Journal of Pharmacology and Experimental Therapeutics(2012), vol. 343, No. 3. pp. 736-745.
Rosas-Ballina, et al., "Acetylcholine-Synthesizing T Cells Relay Neural Signals in a Vagus Nerve Circuit", Science, Oct. 2011, 334(6052); pp. 98-101.
Sara, et al., "Orienting and Reorienting: The Locus Coeruleus Mediates Cognition Through Arousal", Neuron 76, Oct. 2012, Elsevier Inc., pp. 130-141.
Schedel, et al., "Human Platelets Express Functional alpha 7-Nicotinic Acetylcholine Receptors", Arterioscler Thromb Vasc Biol, Apr. 2011, pp. 928-934.
Spark Biomedical Inc., "Transcutaneous Auricular Neurostimulation (tAN™) to Aid in the Reduction of Symptoms Associated With Opioid Withdrawal", Sparrow Clinical Whitepaper, Version: MKT-005-V1, 2021, 8 pages.
Steidel, Kenan, et al., "Transcutaneous Auricular Vagus Nerve Stimulation Influences Gastric Motility: A Randomized, Double-Blind Trial in Healthy Individuals", Elsevier, Brain Stimulation, 2021, pp. 1126-1132.
Stokes, et al., "The Structural Basis for GTS-21 Selectivity between Human and Rat Nicotinic σ 7 Receptors," Molecular Pharmacology (2004), vol. 66, No. 1. pp. 14-24.
Fritz, Jason R., et al., "The Neural Tourniquet", Bioelectronic Medicine1:28-29, 2014 pp. 25-29.
Aryeh Shander, et al., "A new perspective on best transfusion practices" Blood Transfus 2013; 11: 193-202 DOI 10.2450/2012.
Christopher Heeschen, et al., "A novel angiogenic pathway mediated by non-neuronal nicotinic acetylcholine receptors", J. Clin. Invest. 110:527-536 (2002).
W.M. Clark, MD, et al., "A randomized dose-response trial of citicolin in acute ischemic stroke patients", Neurology 1997;49:671-678.
Tomoyuki Abe, et al., "A swine model of acute thrombocytopenia with prolonged bleeding time produced by busulfan", Exp. Anim. 65(4), 345-351, 2016.
Alexander Vang, et al., "7 Nicotinic acetylcholine receptor mediates right ventricular fibrosis and diastolic dysfunction in pulmonary hypertension", JCI Insight 2021;6(12):e.
H. Mitra, P. Jayaram, et al., "Characterization and rheology of platelet-rich plasma", The Society of Rheology, Inc. J. Rheol. 64(5), 1017-1034 Sep. 2020.
A Mike, et al., "Choline and acetylcholine have similar kinetic properties of activation and desensitization on the alpha7 . . . ", Brain Research vol. 882, Nov. 2000 155-168.
Richard J. Radek, et al., "Effects of the Novel a7 Nicotinic Acetylcholine Receptor Agonist ABT-107 on Se . . .", PET 343:736-745, 2012.
Tor Hervig, et al., "Storage and handling of blood components—perspectives", Transfusion and Apheresis Science 51 (2014) 103-106.
Yan Liu, et al., "Choline produces antiarrhythmic actions in animal models by cardiac . . .", PET 343:736-745, 2012.
Julio J. Secades, "Citicoline: pharmacological and clinical review, 2016 update", Rev Neurol 2016; 63 (Suppl 3): S1-S73.
Anastasia N. Sveshnikova, et al., "Compartmentalized calcium signaling triggers subpopulation formation upon platelet activation through PAR1", Mol. BioSys Journ, Jan. 2015.
Alice L. Bodnar,et al., "Discovery and Structure-Activity Relationship of Quinuclidine . . .", J. Med. Chem. 2005, 48, 905-908.
Dong-Jie Li, et al., "Dysfunction of the Cholinergic Anti-Inflammatory Pathway Mediates Organ . . .", Hypertension. 2011;57:298-307.

(56) References Cited

OTHER PUBLICATIONS

B. Yener Arslan, et al., "Effects of Intracerebroventricular Injected Choline on Cardiovascular Functions and Sympathoadrenal . . .", J of Card Pharm 17:814-821.
S . Kooijman,et al., "Hematopoietic a7 nicotinic acetylcholine receptor deficiency increases inflammation and . . .", Journal of Thrombosis and Haemostasis, 13: 126-135.
R. Scott Bitner, et al., "In Vivo Pharmacological Characterizations", JPET 334:875-886 2010.
Robert Freedman, M.D., et al., "Initial Phase 2 Trial of a Nicotinic Agonist in Schizophrenia", Am J Psychiatry 2008; 165:1040-1047.
Akk and Auerbach, "Inorganic, Monovalent Cations Compete with Agonists for the Transmitter Binding Site of Nicotinic Acetylcholine Receptors", Biophysical Journ vol. 70 2652-58.
Jason P. Acker, et al., "Quality Assessment of Established and Emerging Blood Components for Transfusion", Journal of Blood Transfusion, vol. 2016 28 pages.
R. Azuma, et al., "Metabolism and disposition of GTS-21, a novel drug for Alzheimer's disease", Xenobiotica, 99, V 29, No. 7, 747-62.
Clarence H. Brown, III, et al, "Morphological, biochemical, and functional changes in human platelets subjected to shear stress", vol. 86, No. 3.
Allendorf and Brown, "Neu1 Is Released From Activated Microglia, Stimulating Microglial Phagocytosis and Sensitizing Neurons to Glutamate", Original Research May 26, 2022.
Gouri Yogalingam, et al., "Neuraminidase 1 Is a Negative Regulator of Lysosomal Exocytosis", Developmental Cell 15, 74-86, Jul. 2008.
William R. Kem, et al., "Pharmacokinetic Limitations on Effects of an Alpha7-Nicotinic . . ." Neuropsychopharmacology vol. 43, pp. 583-589 (2018).
V. Mahnir, B. Lin, K. Prokai-Tatrai and W.R. Kem, "Pharmacokinetics and Urinary Excretion of Dmxba (GTS-21), a Compound Enhancing Cognition", Biopharm. Drug Dispos. 19: 147-15.
Jooyoung Cho,et al., "Platelet storage induces accelerated desialylation of platelets and increases hepatic . . .", J. Transl Med (2018) 16:199.
Nahreen Tynngård, "Preparation, storage and quality control of platelet concentrates", Transfusion and Apheresis Science 41 (2009) 97-104.
Ann Olincy, MD, et al., Proof-of-Concept Trial of an 7 Nicotinic Agonist in Schizophrenia, Arch Gen Psychiatry/vol. 63, Jun. 2006.
Harumi Kitagawa, et al., "Safety, Pharmacokinetics, and Effects on Cognitive Function of . . .", Neuropsychopharmacology (2003) 28, 542-551.
S. Robinson, et al., "The administration of blood components: a British Society for Haematology Guideline", British Blood Trans. Soc., Nov. 6, 2017.
Patricia Di Ciano, and Barry J Everitt, "The GABAB Receptor Agonist Baclofen Attenuates Cocaine and Heroin-Seeking Behavior by Rats", Neuropsychopharmacology (2003) 28, 510-51.
Dana V. Devine, PhD, and Katherine Serrano, PhD, "The Platelet Storage Lesion", Clin Lab Med 30 (2010) 475-487.
Dianne E. van der Wal, et al., "The role of neuraminidase 1 and 2 in glycoprotein Ib—mediated integrin IIb 3 activation", haematologic 2020; 105(4).
M. Hajos, et al., "The Selective a7 Nicotinic Acetylcholine Receptor Agonist PNU-282987 [N-[(3R)-1-Azabicyclo . . .", JPET 312:1213-1222, 2005.
Clare Stokes, et al., "The Structural Basis for GTS-21 Selectivity between Human and Rot Nicotinic a7 Receptors", Mol Pharmacol 66:14-24, 2004.
Christopher J. Czura ,et al., "Transcutaneous auricular neurostimulation to reduce heavy mentrual . . .", Frontiers, Published Oct. 8, 2025.
Christopher J. Czura, et al., "Vagus Nerve Stimulation Regulates Hemostasis in Swine", Shock, vol. 33, No. 6, pp. 608Y613, 2010.

* cited by examiner

EX-VIVO ENHANCEMENT OF PLATELET FUNCTION DURING BLOOD PROCESSING

RELATED APPLICATIONS

This application is related to U.S. patent application Ser. No. 18/583,160 entitled "Electrical Stimulation Methods and Devices for Improving Blood Management" and filed Feb. 21, 2024 (now U.S. Patent Publication No. 2024/0285944), U.S. patent application Ser. No. 18/926,706 entitled "Electrical Stimulation Methods and Devices for Improving Blood Management" and filed Oct. 25, 2024 (now U.S. Pat. No. 12,390,640), and U.S. patent application Ser. No. 18/807,124 entitled "Electrical Stimulation Methods and Devices for Improving Blood Management" and filed Aug. 16, 2024 (now U.S. Patent Application Publication No. 2024/0399145). The contents of each of the above-referenced applications are hereby incorporated herein in their entireties.

BACKGROUND

Hemostasis, the process by which bleeding is stopped, is generally triggered by molecules that become exposed to circulating blood at a site of vascular injury. Sub-endothelial collagen (SEndC) and Tissue Factor (TF, aka coagulation Factor 3 or fIII) are examples of such molecules. While circulating platelets (i.e., thrombocytes) bind to exposed SEndC, TF binds to a particular circulating molecule called coagulation Factor 7 (fVII). The interaction between TF and fVII leads to the activation of fVII (fVIIa) and to the formation of the TF-fVIIa complex, which is called the Extrinsic Tenase (i.e., Extrinsic Xase). This TF-fVIIa complex initiates what is known as the coagulation cascade by activating coagulation Factor 10 (fX) and coagulation Factor 9 (fIX) into fXa and fIXa respectively (see below). Platelets adhering directly or indirectly to SEndC start to aggregate and form the initial plug to stop the bleeding. This plug is known as the platelet plug or thrombus. The platelet plug is then reinforced by the adherence and crosslinking of fibrin. The process leading to the formation of the platelet plug is commonly referred to as primary hemostasis whereas the process leading to the reinforcement of it by crosslinked fibrin (i.e., activated coagulation factor 1 or fla) is known as secondary hemostasis. Platelets are anucleate blood cells mainly produced in bone marrow from megakaryocytes. Under normal conditions about 100 billion platelets are produced daily, leading to a concentration in blood that ranges between 150 to 400 million per milliliter. Platelets enter the vasculature circuit and, in humans, circulate for approximately 7 to 10 days before being removed by the liver and the spleen. Interestingly, as they circulate, they pool in the spleen where about a third of all circulating platelets are located at any given time. In humans, platelets transit time through the spleen is approximately 30 minutes.

Platelets contain, amongst others, mitochondria and two types of granules, the alpha granules (αG) and the dense or delta granules (δG). Ionized calcium (Ca2+ aka coagulation Factor 4 or fIV), a key component for coagulation, is stored inside the platelet at least within the mitochondria, the Dense Tubular System (DTS), as well as within the delta granules. Platelets circulate in the blood in an inactivated state and as such they do not aggregate; however, platelets become activated when they bind to exposed SEndC following an injury.

Platelets bind to SEndC directly via either the GP VI or the GP Ia/IIa receptors or indirectly through von Willebrand factor (vWF) via GP Ib-V-IX receptor. An activated platelet undergoes a shape change and secretes through its membrane the contents of its granules. The contents of the alpha granules include, among other components, fibrinogen (a.k.a. coagulation factor 1 or fI), platelet-derived growth factor (PDGF), vWF, TGF beta, coagulating Factor 5 (fV), platelet factor 4 (Pf4), and insulin-like growth factor 1 (IGF1). Delta granules (δG) contain, among other components, Ca2+, ADP, ATP, and serotonin (5-HT). Activated platelets promote changes to membrane receptors GP IIb/IIIa (aka integrin αIIbβ3) such that these receptors can bind to vWF as well as to fibrinogen. In addition, Thromboxane A2 (TxA2) is secreted from activated platelets. TxA2, and ADP activate circulating platelets which begin to aggregate with other activated platelets via GP IIb/IIIa-VWF-GP IIb/IIIa and GP IIb/IIIa-fibrinogen-GP IIb/IIIa bridges. This aggregation gives rise to platelet accumulation at the injury site generating the aforementioned platelet plug. This platelet plug, although weak, is the first step in limiting and eventually stopping blood from leaving the vascular system. Clot retraction is greatly influenced by the presence of the GP IIb/IIIa receptor on the platelet surface. Clot retraction assists in healing the wound by bringing the separated edges of the wound closer and closer together until the wound is healed.

As also mentioned earlier, the plug is then reinforced by fibrin fibers and further by the crosslinking of them by activated coagulation Factor 13 (fXIIIa). Fibrin is produced when circulating as well as platelet-secreted fibrinogen is converted into fibrin by thrombin (i.e., activated coagulation Factor2 or fIIa). In turn, thrombin is produced by cleavage from circulating prothrombin (a.k.a. coagulation factor 2-fII). Thrombin can be produced from prothrombin in relatively small amounts by fXa bound to platelet surfaces. Thrombin is not only able to turn fibrinogen into fibrin but it can also activate other platelets as well as convert fV, coagulation Factor VIII (fVIII), coagulation Factor XI (fXI), and coagulation Factor 13 (fXIII) into their activated forms (fVa, fVIIIa, fXIa, fXIIIa respectively). fVa binds to fXa on the platelet surface in a Ca2+ dependent manner to form prothrombinase (fXa-fVa complex). The prothrombinase complex is capable of converting large quantities of prothrombin into thrombin. In fact, the prothrombinase complex cleaves thrombin from prothrombin at a rate that is hundreds of thousands of times faster (e.g., approximately 250,000 times) than fXa alone. Consequently, the presence of prothrombinase on the platelet surface greatly accelerates the coagulation process.

As stated before, fX can be activated into fXa by the Extrinsic Tenase; however, fX can also be activated by the Intrinsic Tenase, which is composed of fVIIIa and fIXa. In order for the Intrinsic Tenase to be assembled, both fVIII and fIX need to be activated. Thrombin can activate fVIII, and the Extrinsic Tenase and fXIa can activate fIX.

Improper blood management can be life threatening. After an injury occurs, the amount of blood lost must be minimized. When bleeding volume is such that it could lead to hypovolemia, then perfusion and oxygenation of tissues, in particular brain tissue, must be enhanced to prevent permanent damage and possible death. Further, some hemorrhages, whether or not they lead to hypovolemia, may lead to sepsis. For all of these reasons, mitigating blood loss is a critical concern in a medical environment.

Platelets transfusions from donors are common practice in any health care system. Platelets are collected from human donors mainly in two forms, via whole blood collection and separation (whole blood-derived platelets) or via an apheresis process (apheresis-derived platelets). In the United States, usually, whole blood-derived platelets contain approximately $5.5\times10^{10}$ platelets per unit and can be constituted from a random mix of platelets from several donors. Platelet donations from whole blood usually yields between 4 to 6 units. Apheresis-derived platelets units contain a minimum of $3\times10^{11}$ platelets and are all from a single donor. Platelets are expensive and essential in any healthcare system. For example, 2 to 2.5 million platelet units are used in the US alone every year, with an acquisition cost per platelet unit of between $500 and $700 and several times more after adding testing, storage, and transfusion costs. Depending on the condition being treated, the cost of a single platelet unit transfusion can reach $10,000. Platelets are stored in different ways; platelets can be lyophilized or put into a solution in platelet-rich mix to be stored. Lyophilized platelets, although lasting much longer, are generally of lower quality and usually require additives before lyophilization in order to prevent damage to cellular and intracellular membranes and constituents; careful rehydration is usually needed in order to properly reconstitute them before transfusion. Platelet-rich solutions produce better quality platelets; however, they are only stored for about 5 days due to potential infection and spontaneous aggregation. Any reduction on the cost of platelets as well as any improvement in the ability to improve storage conditions would be welcomed by any national or private health care system as well as by patients. A cost reduction can be realized by having platelets with higher coagulation efficiency and with a higher platelet yield following storage. In this context, we refer to coagulation efficiency as the ability of a reduced group of platelets to produce a similar clinical outcome to that of a larger group of platelets. That is, fewer platelets are required to achieve the same clinical outcome In related U.S. Pat. No. 12,390,640, the inventors of the present application described how to mitigate blood loss following an injury. In one aspect, the inventors developed systems and methods using auricular neurostimulation for mitigating the possibility of bleeding in a prophylactic manner before any bleeding occurs by increasing an individual's coagulation potential. The auricular neurostimulation enhances platelet function through modulation of spleen activity. Using the proactive mitigation, for example, a patient may be treated prior to a surgical operation so that, in the event of unforeseen blood loss, rapid coagulation could minimize the impact of the event.

Generally, activation and thus aggregation of stored platelets has proved to be problematic, often resulting in reduced shelf life and a loss of up to 25% of functional platelets. Platelet activation during storage in blood banks often leads to unwanted aggregation, which is part of a broader issue known as platelet storage lesion (PSL). This can reduce the platelets' ability to function effectively after transfusion. In another example, whole blood samples are shaken during transportation, resulting in platelet activation. Whole blood samples are also prone to cold-induced platelet activation. Thus, many solutions have been proposed to better protect blood samples against platelet activation.

The inventors recognized a need to translate the in-vivo mechanism to an ex-vivo blood processing environment capable of producing blood-banked platelets with enhanced coagulation capabilities to accelerate bleeding cessation in emergency medical environments and to reduce the number of platelets needed during platelet transfusions by having more efficient platelets; i.e., using lower platelet quantities that can produce the same clinical outcome that the typical platelets numbers (lower platelet concentrations achieving clinical effects typically requiring higher platelet concentrations). Further, the inventors recognized the need to enhance the platelet coagulation capabilities in a controlled manner that arrests the potential for activating it in a stored blood sample or platelet-rich mix, thereby mitigating against degradation of the product.

SUMMARY OF ILLUSTRATIVE EMBODIMENTS

Aspects of the present disclosure relate to producing platelets with enhanced coagulation capabilities using ex-vivo equipment and methods. Whole blood extracted from a subject may be enhanced with capabilities promoting a faster and/or more efficient coagulation at an injury site. The platelets, for example, may be separated from the whole blood stored for later use in transfusions in a surgical (e.g., organ transplant or heart surgery), emergency medical scene (e.g., in trauma or burn patients), in a patient undergoing chemotherapy, or in a combat environment. In some embodiments, the platelets may be enhanced and returned to the subject's blood stream in a closed-circuit enhancement system such as, for example, when using an apheresis machine. Enhanced platelets (primed platelets) may be particularly beneficial for recipients with coagulation deficiencies, such as subjects with hemophilia A, hemophilia B, hemophilia C, or von Willebrand disease (vWD). In another example, enhanced platelets may be provided to patients to overcome effects of an anticoagulant medication in the subject's system.

Producing more efficient platelets which have enhanced coagulation capabilities, in particular at an injury site, in some embodiments, involves activating platelet cholinergic receptors in whole blood. The activation may produce enhanced platelets without triggering platelet activation that may result in shorter shelf life and/or reduced usability of the whole blood or platelets harvested therefrom.

In some embodiments, producing primed platelets involves introducing at least one reagent into collected whole blood. The reagent, for example, may trigger processes within the whole blood that mimics natural physiological enhancement (e.g., as performed in the spleen with methods described in U.S. Pat. No. 12,390,640). The reagent (s) may be introduced into the whole blood using common hospital equipment. Some reagents may include $CaCl2$ (to increase the $Ca2+$ concentration) and a cholinergic receptor agonist or partial agonist, for example GTS-21. In the detailed disclosure, both agonists and partial agonists are referred to using the term "agonist."

In other embodiments, producing platelets with enhanced coagulation capabilities at injury sites involve, as before, activating cholinergic receptors on the platelets using a cholinergic receptor agonist in the presence of a desired concentration of $Ca2+$. In this case, platelets can be in a liquid mixture with a high platelet concentration. The liquid mixture may be, in some examples, a platelet-rich plasma (PRP) or other natural or artificial liquid with a platelet-rich mix, such as a platelet additive solution (PAS). Under this scenario, $Ca2+$ and a cholinergic receptor agonist would be added to the platelet-rich mix resulting in an enhanced platelets population (a.k.a. primed platelets) without triggering platelet activation which may result in shorter shelf life and/or reduced usability of the harvested platelets.

By storing primed platelets, either in whole blood form or in a separated form (e.g., in a platelet-rich mix), the platelets may be later used to perform blood or platelet transfusions. Through introducing the primed platelets into a patient's blood stream, the coagulation process at an injury site is fast-tracked, thereby resulting in a smaller volume of blood loss and/or a quicker cessation in bleeding as compared to performing a transfusion with conventional stored blood product. In another approach, primed platelets, which are more efficient, may be provided to a patient with a goal of obtaining a typical coagulation time (e.g., in which a faster coagulation is not necessarily desired or immediately needed), while lowering a total number of platelets needed. Thus, such a platelet transfusion may provide an equivalent clinical outcome with less platelets. In this manner, the number of platelet units required in a given patient may also be reduced.

The foregoing general description of the illustrative embodiments and the following detailed description thereof provide mere examples of various aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. In the drawings.

DETAILED DESCRIPTION OF ILLUSTRATIVE EMBODIMENTS

Figure 1A:
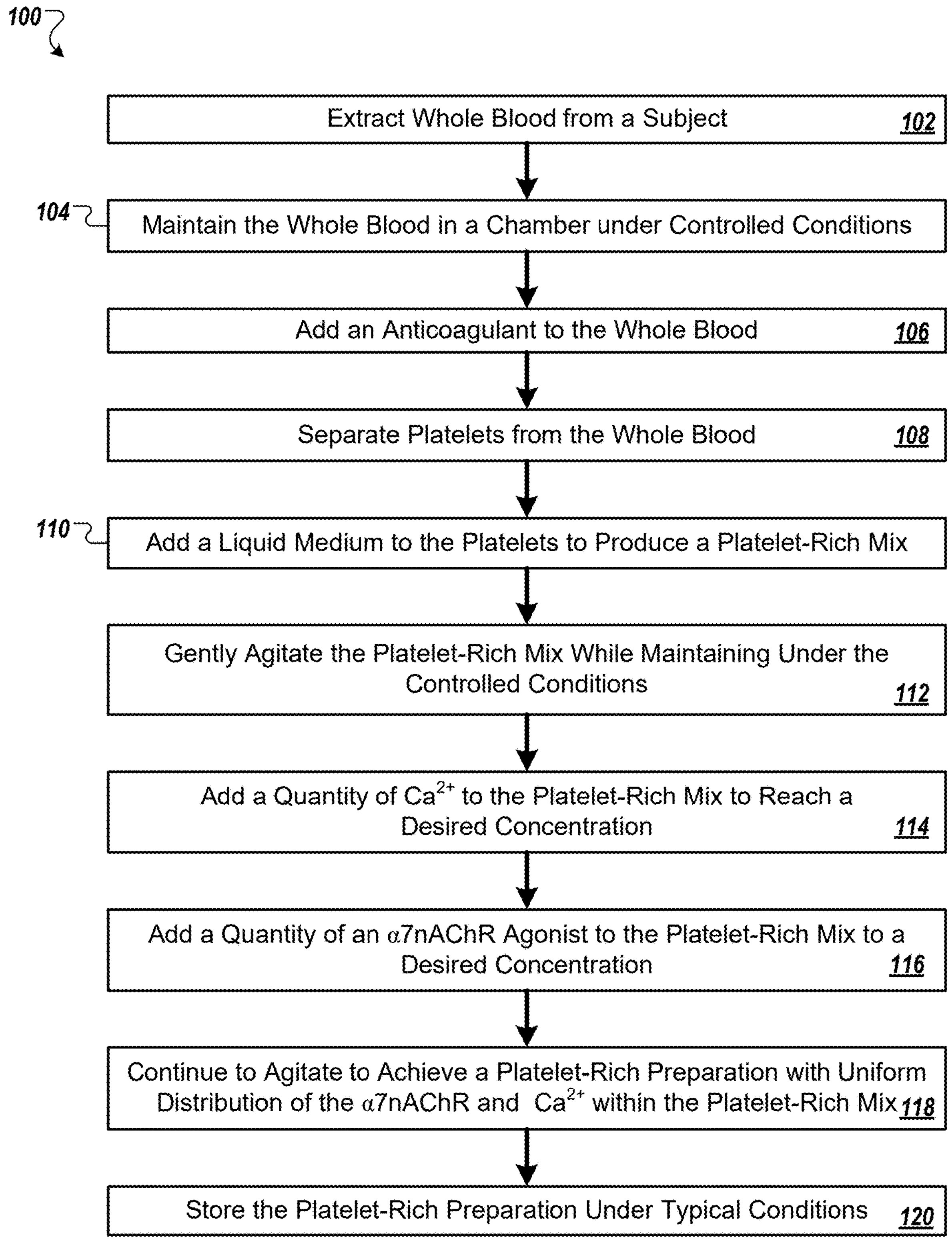
FIG. 1A is a flow chart of an example method for ex vivo enhancement of platelet function for blood banking applications.

The description set forth below in connection with the coordinating drawings is intended to be a description of various illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

As used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Further, the terms "approximately," "about," "proximate," "minor variation," and similar terms generally refer to ranges that include the identified value within some margin, such as, in some examples, 20%, 10%, or 5% in certain embodiments, as well as any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Hemostasis

Figure 2:
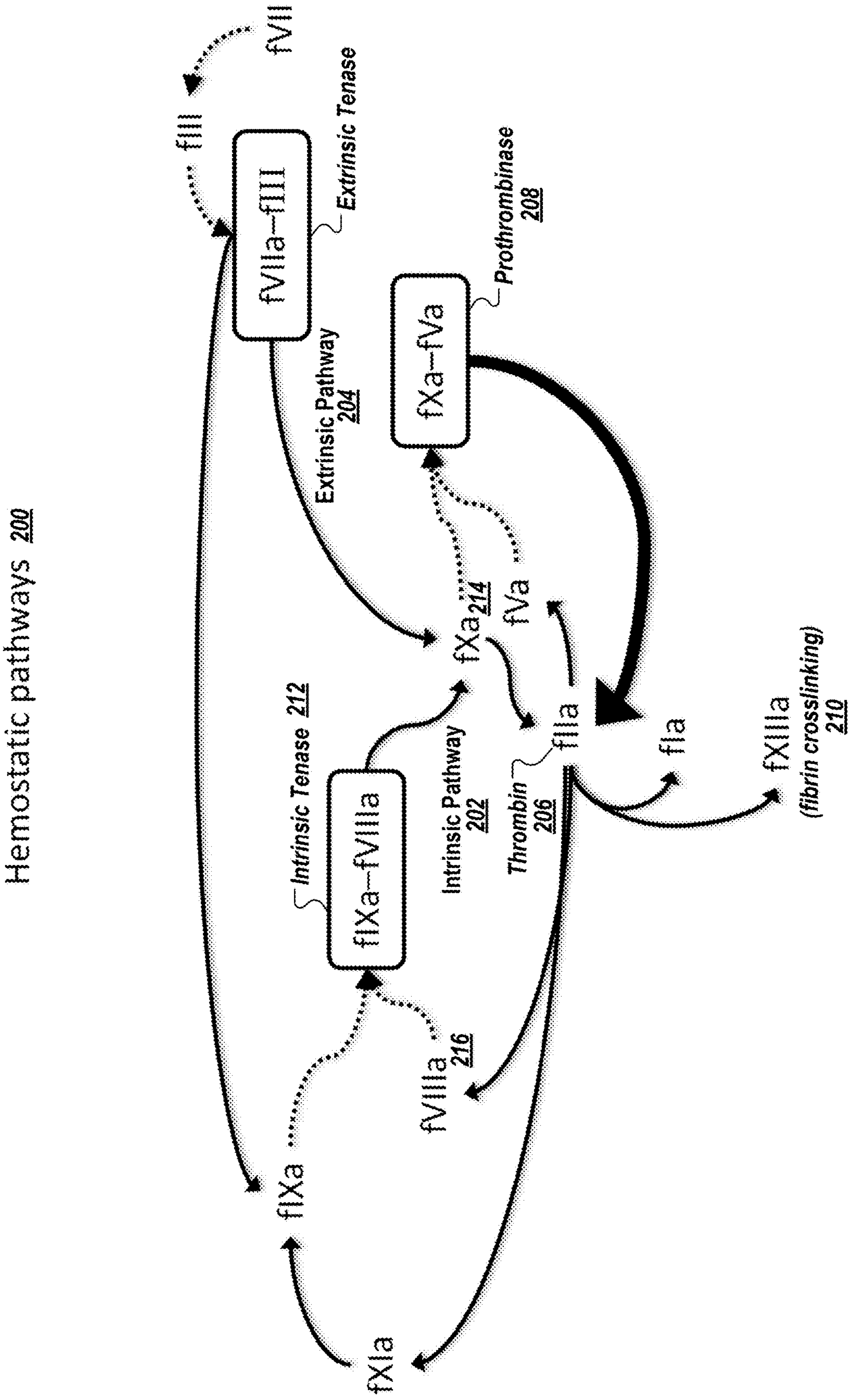
FIG. 2 is a block diagram of example hemostatic pathways.

Turning to FIG. 2, a diagram of the hemostatic pathways 200 is illustrated. The pathway in which fXa is activated by the Extrinsic Tenase is generally known as the Extrinsic Pathway 204, and that in which fXa 214 is activated by the Intrinsic Tenase is called the Intrinsic Pathway 202. The coagulation steps after the activation of fXa 214 until the fibrin crosslinking by fXIIIa 216 are termed the Common Pathway. Important to note is the remarkable quantitative difference between the Intrinsic Pathway 402 and Extrinsic Pathway 404. Under normal circumstances, compared to the Extrinsic Pathway 404, thrombin 406 is produced between 50 to 100 times faster via the Intrinsic Pathway 402. Thus, it would be reasonable to state that under normal conditions the Extrinsic Pathway 404 initiates the hemostatic process, but it is the Intrinsic Pathway 402 that gets it to the finish line.

Platelets are not homogeneous; they exhibit marked differences which become evident after platelet activation during hemostasis. One of the most consequential differences amongst platelets subpopulations is that some activated platelets become procoagulant (although under debate, some refer to them as procoagulant collagen- and thrombin-activated or COAT platelets) while others activate into noncoagulating platelets (pro-aggregatory platelets). Whereas most of the thrombin 406 is produced by procoagulant platelets, noncoagulating platelets are more prone to aggregate; thus, both types are needed for proper coagulation. Although there is large variability from subject to subject, on average, only 30% of activated platelets become procoagulant platelets.

In many or possibly all cases, procoagulant platelets swell and their phospholipid membrane becomes more negative due to exposure of phosphatidylserine (PS) on their membrane surface. Platelet membranes becoming more negative results in a significant increase in the binding affinity of prothrombinase to them; thus, prothrombinase 208 is much more likely to bind to procoagulant platelets (pCP) than to noncoagulating (nCP) ones. Since, as mentioned before, prothrombinase 208 can produce thrombin 206 up to two hundred and fifty thousand times (250,000 times) faster than fXa alone, it is clear that most of the thrombin 206 at or near the injury site will be produced on pCP.

Given the hemostatic processes discussed above, it is evident that even small increases in the pCP/nCP ratio can increase the rate of thrombin production at or near the injury site, thus accelerating platelet and fXIII activation as well as fibrin production. Thus, in addition to leading to faster platelet aggregation, increases in thrombin generation also leads to increases in the rate of fibrin binding and crosslinking 210 which altogether promotes shorter bleeding times and lower bleeding volumes.

Further, faster/higher production of thrombin 206 at the injury site can compensate deficits and limitations in the hemostasis process (e.g., bleeding/coagulation disorders), such as, for example, a lower production or a lack of Intrinsic Tenase 212 production due to deficiencies or lower than normal (including complete lack of) fVIII, fIX, or fXI, which is respectively the case in Hemophilia A, Hemophilia B, and Hemophilia C. Interestingly, studies have shown that, compared with healthy individuals, the levels of pCP is significantly lower in individuals suffering from hemophilia. As mentioned earlier, vWF facilitates platelet adhesion to endothelial tissue at an injury site as well as it supports platelet-to-platelet adhesion after platelet activation at or near an injury site. In addition, vWF serves as a carrier for fVIII in plasma in the form of a vWF-fVIII complex. Consequently, lower amounts of circulating/available fVIII are also seen in vWD type 2N. Since a faster/higher production of thrombin 206 leads to a higher platelet activation rate, and thus to a higher fibrinogen release rate, another circumstance leading to a deficiency and/or limitation in the hemostasis process that could be compensated by faster/higher production of thrombin 206 at or near the injury site is when there is a lower platelet adhesion and aggregation due to a lower count or lack of available or fully functional vWF such as for example, in vWD type 1, type 2A, type 2M, and type 3. Yet another example in which higher/faster thrombin production can compensate for existing deficiencies in hemostasis is in the case of vWD type 2B, which leads to both lower adhesion/aggregation of platelets as well as a lower platelet count. By compensating it is not suggested that in any of the cases the hemostasis process would be restored to what would be expected in a normal subject (e.g., where deficits and limitations are not present). Instead, the term compensate is used to refer to a significantly faster hemostasis process than that which otherwise occurs in light of the deficiencies and limitations without the extra amount of thrombin 206 present. One manner in which this compensation may occur is by locally increasing the ratio of procoagulant/anticoagulant activity at or near the injury site.

A strong activation is necessary for a platelet to activate as a procoagulant platelet (pCP); however, this is not sufficient. Experiments using double agonist (e.g., collagen and thrombin) have been shown to produce a small percentage of platelet activation into procoagulant types. Some have suggested that the COAT acronym is inaccurate since not only is activation by both collagen and thrombin insufficient to provide a considerable boost in platelet activation into procoagulant types, but it is also not unique. It is not unique in the sense that a very large concentration of thrombin 2-6 can also activate platelets into procoagulant types. Several elements have been identified as contributing factors to determining whether or not, upon activation, a platelet becomes procoagulant. Some of these elements include platelet age, size, number of mitochondria, number as well as content of granules, and baseline $Ca^{2+}$ concentration. Interestingly, under similar circumstances, younger platelets are more likely to become procoagulant than older ones (as stated earlier, in humans, platelets circulate for about 7 to 10 days before being removed by the liver and/or spleen).

Ex-Vivo Enhancement of Platelet Function

Figure 1B:
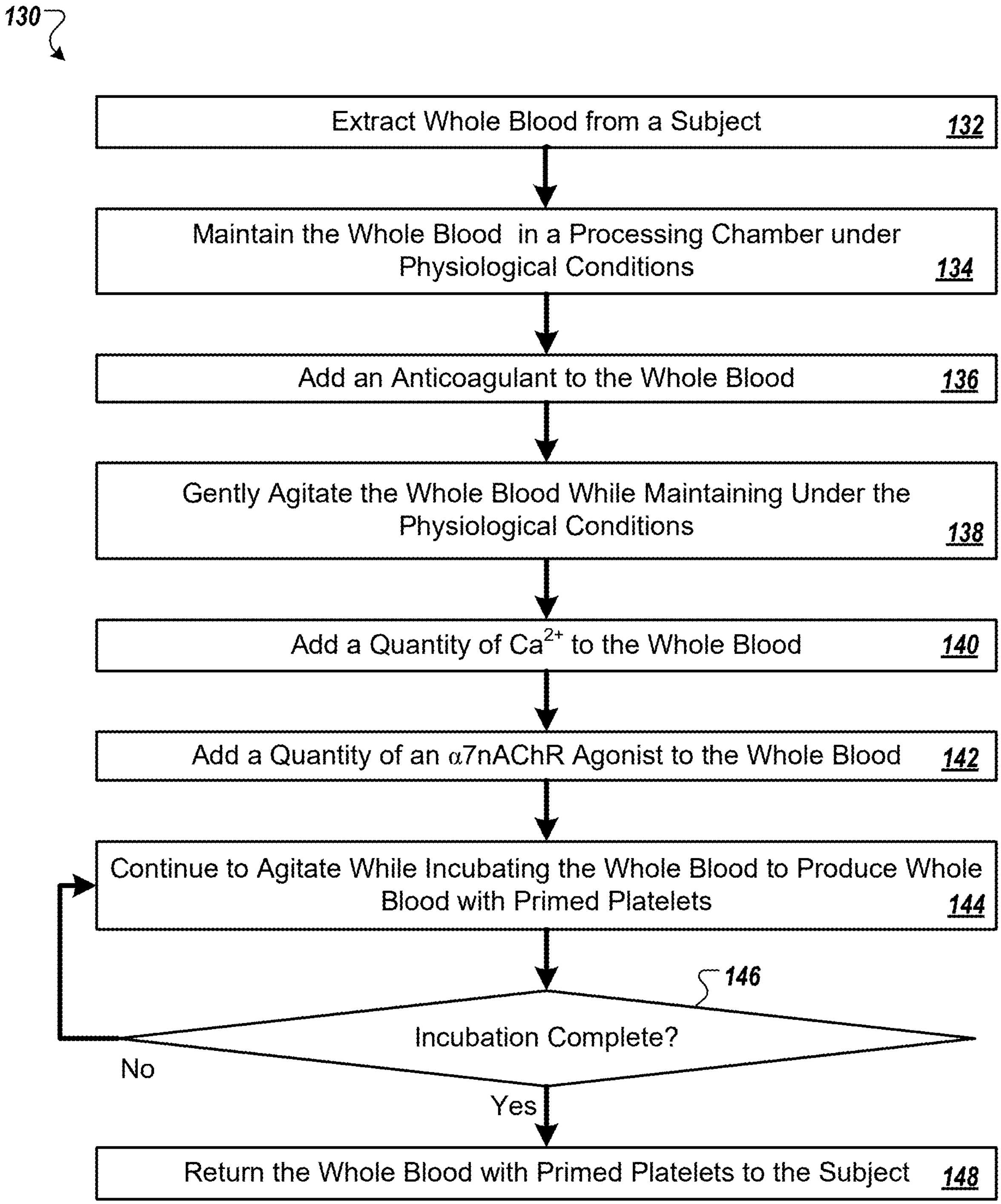
FIG. 1B is a flowchart illustrating an example method for ex vivo enhancement of platelet function in an autologous closed-circuit application.
Figure 1C:
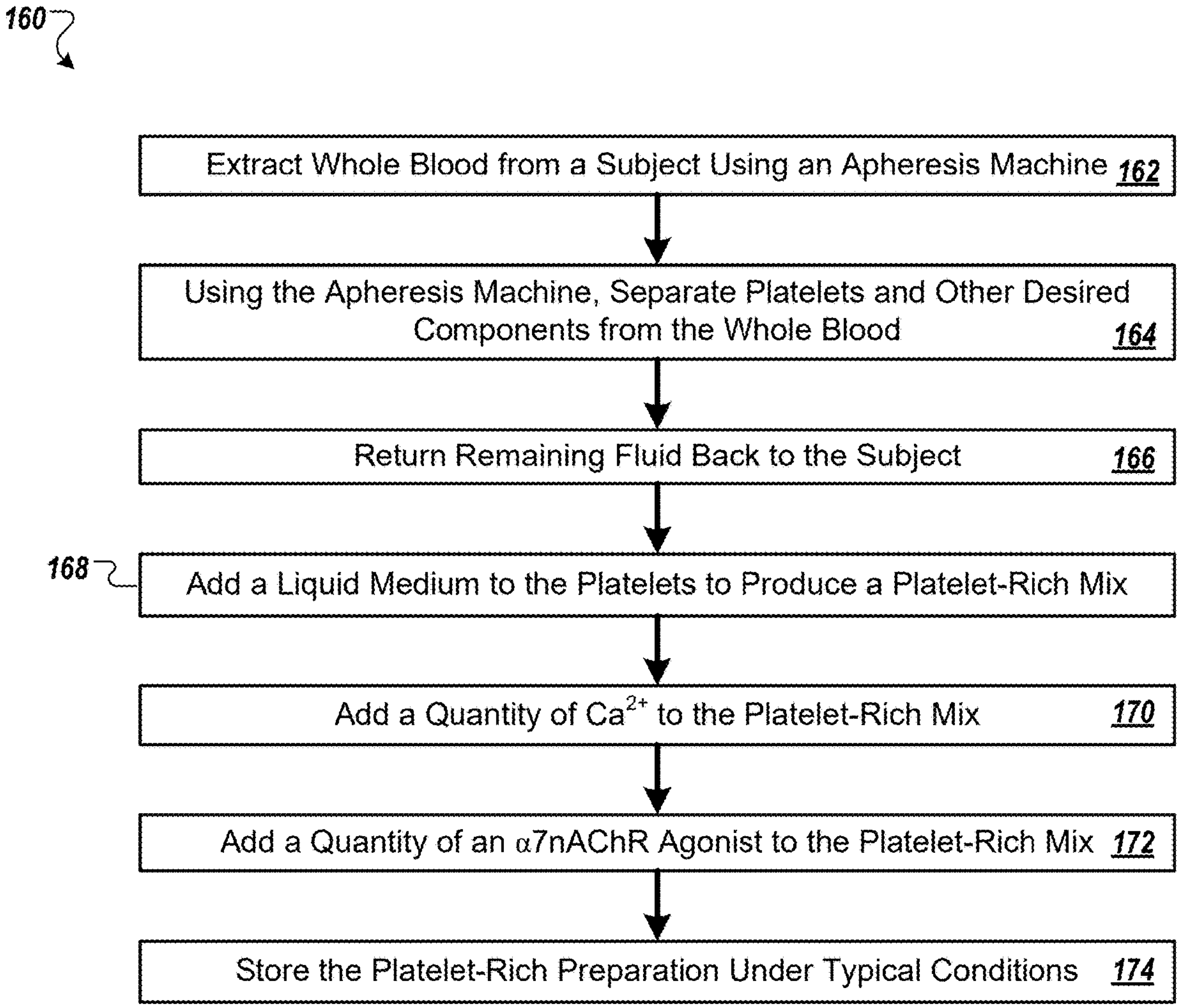
FIG. 1C is a flowchart illustrating an example method for ex vivo enhancement of platelet function using apheresis collection.

Three flowcharts, FIGS. 1A, 1B, and 1C, illustrate example methods for ex vivo enhancement of platelet function using the natural function of the hemostatic pathways 200 described above in relation to FIG. 2. The methods differ based on the intended application: blood banking storage (FIGS. 1A and 1C) versus autologous closed-circuit immediate return to the subject (FIG. 1B). Each method involves treating platelets with calcium ions ($Ca^{2+}$) and an α7nAChR agonist, but the timing and handling differ based on whether the platelets will be stored or immediately reinfused. Each method may be performed, for example, as part of a standard process involving blood extraction from a subject. At least a portion of each of the methods described below may be automatically controlled by processing circuitry, such as a controller of a whole blood processing system configured for enhancing platelet function of blood extracted from a mammal, such as a human.

Turning to FIG. 1A, an example method 100 for preparing enhanced platelets from whole blood for blood banking applications is illustrated.

In some implementations, the method begins with extracting whole blood from a subject (102). The whole blood may be collected, for example, using conventional blood collection techniques, such as those used by blood banks. The whole blood may be collected in blood collection bags or vials. In another example, the whole blood may be transferred directly from the circulatory system of the patient to a processing chamber.

In some implementations, the whole blood is maintained in a processing chamber under controlled conditions (104). The controlled conditions, in some examples, may include gentle agitation (e.g., 60-70 RPM) and/or controlled temperature (e.g., 20-38° C.).

In some implementations, while the whole blood is maintained in the processing chamber, an anticoagulant is added to the whole blood (106). The anticoagulant, for example, may be used to prevent premature coagulation.

In some implementations, the platelets are separated from the whole blood (108). Separation may be performed using standard blood separation equipment such as centrifugation. The platelets may be considered, at this point, to be a platelets concentrate, having a high concentration of platelets in a plasma base.

In some implementations, after separation, a liquid medium is added to the platelets to produce a platelet-rich mix (110). The liquid medium, in some examples, may be a platelet additive solution or plasma.

In some implementations, the platelet-rich mix is gently agitated while maintaining the platelet-rich mix under the controlled conditions (112). The agitation, for example, may continue to be performed between 60-70 RPM.

In some implementations, a quantity of $Ca^{2+}$ is added to the platelet-rich mix to reach a desired concentration (114). The $Ca^{2+}$ may be provided, for example, by one or more of the calcium sources illustrated in Table 1, below (e.g., $CaCl_2$) or Calcium Gluconate). In some embodiments, if the liquid medium contains a portion of baseline $Ca^{2+}$, (e.g., PAS below), a volume of $Ca^{2+}$ reagent added to the platelet-rich mix may be adjusted according to the baseline $Ca^{2+}$ included in the liquid medium added in operation 110. The $Ca^{2+}$ may be injected into the chamber in one or more controlled volumes. Options for calcium sources and corresponding volumes are provided in Table 1, below. In some implementations, the quantity is added until a desired concentration is achieved, such as 1.5 millimolar (mM).

TABLE 1

Example Calcium Source Options

| Calcium Source | Molecular Weight | To achieve 1.5 mM in 300 mL | Notes |
|---|---|---|---|
| Calcium Chloride ($CaCl_2$•$2H_2O$) | 147.01 g/mol | 66.2 mg (or 4.5 mL of 100 mM stock) | Most common |
| Calcium Gluconate | 430.37 g/mol | 193.7 mg | Gentler |
| Baseline $Ca^{2+}$ in Platelet Additive Solution (PAS) | N/A | ~1.0-1.3 mM already present | Only add ~0.2-0.5 mM additional |

In some implementations, a quantity of an α7nAChR agonist is added to the platelet-rich mix (116). The α7nAChR agonist, for example, may include one or more of the agonists listed in Table 2, below, such as GTS-21. The volume of a7nAChR agonist added may be determined, for example, using Table 3 below. The desired concentration, for example, may be within a range of 10-20 micromolar (μM). Preferably, in some embodiments, a concentration around 15 μM may be achieved.

TABLE 2

Example Agonist Selection Criteria

| Agonist | Human α7 Potency ($EC_{50}$) | Half-life (T½) (hrs) | Clinical Data | Preferred for |
|---|---|---|---|---|
| GTS-21 | Ki = 2.0 ± 0.14 μM<br>$EC_{50}$ ≈ 10 ± 2 μM<br>Partial agonist (~70% efficacy) | 0.76-0.93 (human) | Phase 2 trials completed | Storage application |
| 4-OH-GTS-21 | Ki ~2 μM (similar to parent)<br>Higher efficacy than parent<br>Partial agonist | 0.81-1.18 (as metabolite) | As GTS-21 metabolite | High potency applications |
| PNU-282987 | Ki = 27 nM (rat brain)<br>$EC_{50}$ = 154 nM (chimera)<br>Full agonist | Not determined | Preclinical only | Research and/o validation studies |
| ABT-107 | Ki = 0.2-0.6 nM ([$^3$H]A-585539)<br>Ki = 7 nM ([$^3$H]MLA)<br>$EC_{50}$ = 50-90 nM<br>Full agonist (~80% efficacy) | ~0.9 (calculated from plasma decay) | Phase 1 trials | Alternative (e.g., if GTS-21 unavailable) |

Adding the α7nAChR agonist provides dual benefits: platelet priming and reduction of spontaneous aggregation/activation during storage. Additional considerations for selection and volume control of reagents are presented in Table 3, below.

TABLE 3

Example Primary Reagents for Platelet Enhancement

| Reagent | Vehicle/ Form | Working Concentration | Stock Concentration (Suggested) | Volume to Add (per 300 mL unit) |
|---|---|---|---|---|
| GTS-21 (DMBX-A) | DMSO or sterile water | 10-100 μM (preferred: 50 μM) | 10 mM in DMSO | ~1.5 mL of 10 mM stock |
| 4-OH-GTS-21 | DMSO or sterile water | 10-100 μM (preferred: 50 μM) | 10 mM in DMSO | ~1.5 mL of 10 mM stock |
| PNU-282987 | DMSO | 5-10 μM (preferred: 10 μM) | 10 mM in DMSO | ~300 μL of 10 mM stock |
| ABT-107 | DMSO | 2-10 μM | 10 mM in DMSO | Variable |
| Calcium Chloride ($CaCl_2$) | Sterile saline or WFI | 1.0-2.5 mM $Ca^{2+}$ (preferred: 1.5 mM) | 100 mM $CaCl_2$ stock | |

There are various factors to weigh in selecting a reagent. However, all reagents should be pharmaceutical grade or blood banking grade, and sterile techniques should be applied throughout. Reagent GTS-21, at the time of filing, is considered to be the preferred agonist due to its pharmacokinetic data, having a half-life of about one hour in humans. Further, GTS-21 has passed phase 2 clinical trials. Agonist 4-OH-GTS-21 is an active metabolite of GTS-21, more potent on human α7. Thus, 4-OH-GTS-21 may be preferred in high potency applications. Agonist PNU-282987 was used in a preclinical study in 2015 by Kooijman; thus it is listed as an option but at this time additional safety data would be desirable. See Kooijman, Sander, et al. "Hematopoietic α7 nicotinic acetylcholine receptor deficiency increases inflammation and platelet activation status, but does not aggravate atherosclerosis." Journal of Thrombosis and Haemostasis 13.1 (2015): 126-135. Agonist PNU-282987 is a good candidate for research and/or validation studies. ABT-107, due to its lengthier half-life, is considered an alternative should GTS-21 be unavailable.

In determining volumes to add, the baseline Ca2+ in the storage medium should be accounted for as an adjustment in delivery volume.

For platelet priming, the $Ca^{2+}$ and the α7nAChR agonist activate a cholinergic pathway in the whole blood. The cholinergic pathway, for example, may control the release of Acetylcholine (ACh), such as the α7-Nicotinic Acetylcholine Receptor discussed below.

Data from a study by Abbasian and colleagues showed that the cytosolic $Ca^{2+}$ concentration ($[Ca^{2+}]_{cyt}$) in pCP was at least 50 times higher than the $[Ca^{2+}]_{cyt}$ in nCP (>100 nM vs. 1-2 nM). See Abbasian, Nima, et al. "Supramaximal calcium signaling triggers procoagulant platelet formation." Blood Advances 4.1 (2020): 154-164. Most platelets can activate as pCP if treated with $Ca^{2+}$; however, in general, most platelets activate as nPC if stimulated with some platelet activators. This suggests that $[Ca^{2+}]_{cyt}$ is one, if not the most significant, factor in determining if a platelet activates as a pCP or as a nCP.

Platelets have several transmembrane $Ca^{2+}$ channels which allow $Ca^{2+}$ exchange between extracellular and intracellular spaces (see table below). More than one of these channels or a combination of them could be activated to allow a net positive $Ca^{2+}$ influx, thus incrementing the total amount of $Ca^{2+}$ in the platelet. Within the platelet, this $Ca^{2+}$ is usually taken by one or various mechanisms into internal storages, amongst which are the mitochondria, the dense tubular system (DTS), lysosomes, and the δG. A high $[Ca^{2+}]_{cyt}$ could lead to platelet activation, which if it happens at a location other than at an injury site, may lead to an undesired thrombotic event. Thus, it is important that $Ca^{2+}$ is sequestered into internal (e.g., intracellular) storages such that it is only released into the cytosolic space upon an injury-related activation. This could be achieved in different ways; for example, by inducing an influx of $Ca^{2+}$ into the platelet by activating one of the transmembrane $Ca^{2+}$ channels and temporarily or transiently blocking or partially blocking the mechanisms responsible for the release of $Ca^{2+}$ from internal storages into the cytosolic space. This rise in baseline $Ca^{2+}$ (e.g., total intracellular pre-activation $Ca^{2+}$ not in the cytosolic space) can increase the likelihood of higher $[Ca^{2+}]_{cyt}$ upon activation, thereby incrementing the overall probability for platelets to activate as pCP, leading to a higher coagulation potential. In the event of an injury, a higher coagulation potential translates, on an individual basis, to a higher thrombin production at the injury site. A higher than otherwise production of thrombin at an injury site translates into a faster and localized platelet activation as well as fibrin adhesion and crosslinking onto the thrombus. Therefore, a higher coagulation potential can result in a faster coagulation process leading to lower bleeding volumes and shorter bleeding times.

TABLE 4

Platelet Transmembrane Calcium Channels
Platelet Transmembrane Calcium Channel Table

| Channel | Calcium flow |
|---|---|
| α7-Nicotinic Acetylcholine Receptor (α7-nAChR/nAChRα7) | IN |
| calcium-release activated calcium modulator 1 (CRACM1 or Orai1) | IN |
| Canonical Transient Receptor Potential 6 (TRPC6) | IN |
| Purinergic receptor, P2X1 | IN |
| $Na^{+}/Ca^{2+}$ exchanger | IN |
| plasma membrane $Ca^{2+}$ ATPases (PMCAs) | OUT |

As shown by Schedel and colleagues, platelets express the α7-Nicotinic Acetylcholine Receptor (α7nAChR). See Schedel, Angelika, et al. "Human platelets express functional α7-nicotinic acetylcholine receptors." Arteriosclerosis, thrombosis, and vascular biology 31.4 (2011): 928-934. Since the autonomic nervous system (ANS) can control the release of Acetylcholine (ACh), and given that the α7nAChR is a transmembrane $Ca^{2+}$ channel, the presence of α7nAChR on the platelet membrane suggests that platelet $Ca^{2+}$ influx can be modulated by the ANS. Further, since Bennett, et al. showed that ACh inhibits platelet activation, it follows that ACh or another α7nAChR agonist can be used to increase $Ca^{2+}$ via the α7nAChR while preventing platelet activation. See Bennett J A, Ture S K, Schmidt R A, Mastrangelo M A, Cameron S J, Terry L E, Yule D I, Morrell C N, Lowenstein C J. Acetylcholine Inhibits Platelet Activation. J Pharmacol Exp Ther. 2019 May; 369(2):182-187. Since activation of α7nAChR may prevent platelet activation, shelf life and/or the yield of the stored blood product, in particular platelets, can be improved.

In some implementations, the platelet-rich mix continues to be gently agitated to achieve a platelet-rich preparation with uniform distribution of the α7nAChR and $Ca^{2+}$ reagents (118).

In some implementations, the platelet-rich preparation is stored under typical conditions (120). The platelet-rich preparation, for example, may be transferred directly to platelet storage as one or more blood component units. The platelet-rich preparation, for example, may be stored in gas-permeable bags under gentle agitation (e.g., 60-70 RPM) and controlled temperature (e.g., 20-38° C.). In illustration, the platelet-rich preparation may be stored within a room temperature range of about 20-25° C. Typical storage, for example, may involve a storage period of one day to two weeks. Conventionally, platelets are generally stored for around five days. However, platelets may be stored for up to two weeks in extended cold storage. Table 5, below, lists example typical storage conditions.

TABLE 5

Example Post-Treatment Storage Conditions

| Platelet Storage Condition | Temperature | Duration | Agitation |
|---|---|---|---|
| Standard (Preferred) | 20-24° C. | 5-7 days | Continuous gentle |
| Extended Cold | 2-6° C. | Up to 14 days | Optional |

The method 100 does not require a separate incubation step after the reagents have been added, although incubation is possible if desired for another purpose. The platelet storage conditions, including the controlled temperature and gentle agitation, provide the necessary environment for α7nAChR activation and platelet priming to occur. Platelet priming should occur, for example, during the first two to ten minutes of storage. The α7nAChR agonist remains in the platelet-rich preparation throughout the storage period.

The platelet-rich preparation, for example, may be used for performing transfusions in a number of circumstances. Due to the primed platelet content, the platelet-rich preparation, when introduced into a patient, may activate within a region of a wound and accelerate clotting, thereby reducing blood loss and, in at least some circumstances, allowing medical personnel to provide a smaller volume of blood product and/or a fewer transfusions to the patient.

Although described in relation to a particular set of operations, in other embodiments, the method 100 may include more or fewer operations. For example, in some embodiments, an anticoagulant is not added (106). Further, although described in relation to a particular series of operations, in further embodiments, certain operations may be performed in a different order and/or at least partially concurrently. For example the α7nAChR and $Ca^{2+}$ may be premixed together and added at a same time. In further embodiments, α7nAChR, $Ca^{2+}$, and liquid medium may be pre-formulated for introduction to the platelets. In other embodiments, the α7nAChR (116) and $Ca^{2+}$ (114) may be added in smaller volumes, allowing for reaction prior to introduction of the liquid medium (110). Other modifications to the method 100 are possible.

Turning to FIG. 1B, a flow chart of a method 130 illustrates an autologous closed-circuit application for ex-vivo enhancement of platelet function. The application described by the following operations is suitable for procedures such as intraoperative blood salvage or therapeutic apheresis.

In some implementations, the method 130 begins with extracting whole blood from the subject. The blood may be extracted, for example, using an autologous closed circuit transfusion system.

In some implementations, the whole blood is maintained in a processing chamber under physiological conditions (134). The chamber may be a chamber of the autologous closed circuit transfusion system. The physiological conditions may be similar to those described in relation to operation 104 of the method 100 of FIG. 1A. In some embodiments, the physiological conditions include a physiological temperature range of about 36-38° C.

In some implementations, an anticoagulant is added to the whole blood (136), for example as described in relation to operation 106 of the method 100 of FIG. 1A.

In some implementations, the whole blood is gently agitated while maintaining it under the physiological conditions (138). The agitation, for example, may be similar to that described in relation to operation 112 of the method 100 of FIG. 1A.

In some implementations, a quantity of $Ca^{2+}$ is added to the whole blood until a desired concentration is achieved (140), as described in relation to operation 114 of the method 100 of FIG. 1A. The desired concentration, for example, may be around 1.5 mM.

In some implementations, a quantity of an α7nAChR agonist is added to the whole blood until a desired concentration is achieved (142). The α7nAChR agonist may be added, for example, in a manner similar to that described in relation to operation 116 of the method 100 of FIG. 1A. The concentration, for example, may be around 40-60 μM.

In some implementations, the whole blood is agitated while incubating to produce whole blood with primed platelets (144). For example, a dedicated incubation period may be performed after reagent addition to allow for the priming process to function. The incubation period, for example, may last for about five to thirty minutes. Unlike the method of 100 where the storage environment of the platelet preparation provides a built-in incubation period prior to use, incubating the whole blood in the autologous closed-loop application allows for platelet priming.

Once incubation is completed (146), the whole blood with primed platelets is returned to the subject (148). The α7nAChR agonist is also transfused with the whole blood, allowing the primed platelets to progressively gain full functional responsiveness post-transfusion. The α7nAChR agonist clears from the recipient's circulation over time. For example, the GTS-21 agonist has a half-life of approximately one hour.

Although described in relation to a particular set of operations, in other embodiments, the method 130 may include more or fewer operations. For example, in a different embodiment, platelets are separated from the whole blood (e.g., as described in relation to operation 108 of the method 100 of FIG. 1A) such that the $Ca^{2+}$ (140) and the α7nAChR agonist (142) are added to a platelet concentrate or a platelet-rich mix (e.g., including a liquid medium as described in relation to operation 110 of the method 100 of FIG. 1A). Further to this example, the platelet concentrate or platelet-rich mix may be incubated (144) rather than whole blood, and the platelet concentrate or platelet-rich mix may be returned (148), alone or mixed with the rest of the subject's blood, to the subject upon completion of incubation (146). In further embodiments, an anticoagulant may not be added to the whole blood 136, for example in circumstances where the patient is on blood thinners.

Further, although described in relation to a particular order of operations, in other embodiments, certain operations of the method 130 may be performed in a different order and/or concurrently. For example, the $Ca^{2+}$ and the α7nAChR may be added simultaneously or pre-mixed and added as a mix. Other modifications of the method 130 are possible.

Turning to FIG. 1C, a flow chart illustrates a method 160 for preparing enhanced platelets using apheresis collection followed by storage. Apheresis allows for selective collection of platelets while returning other blood components to the donor.

In some implementations, the method 160 begins with extracting whole blood from a subject using an apheresis machine (162).

In some implementations, the platelets are separated from the whole blood using the apheresis machine (164). Further, the apheresis machine may separate other desired blood components from the whole blood during the collection process.

In some implementations, the remaining fluid is returned to the subject via the apheresis machine (166). The return of fluid, for example, marks the completion of platelet donation. Typically, the returned fluid includes red blood cells and most of the plasma.

In some implementations, a liquid medium is added to the platelets to produce a platelet-rich mix (168). The liquid medium, for example, may be similar to that described in relation to operation 110 of the method 100 of FIG. 1A.

In some implementations, a quantity of $Ca^{2+}$ is added to the platelet-rich mix until desired concentration is achieved (170), as described in relation to operation 114 of the method 100 of FIG. 1A. The desired concentration, for example, may be around 1.5 mM.

In some implementations, a quantity of an α7nAChR agonist is added to the platelet-rich mix until a desired concentration is achieved (172). The α7nAChR agonist may be added, for example, in a manner similar to that described in relation to operation 116 of the method 100 of FIG. 1A. The concentration, for example, may be around 40-60 μM.

In some implementations, after the addition of the $Ca^{2+}$ and α7nAChR reagents, the platelet-rich preparation is stored under typical conditions (174). For example, the platelet-rich preparation may be transferred directly to storage including gentle agitation (e.g., 60-70 RPM) and controlled temperature (e.g., 20-24° C.). The platelet-rich preparation may be stored in gas-permeable bags. The storage conditions provide the environment for α7nAChR activation and platelet priming during the initial minutes of storage, such that incubation is unnecessary. The α7nAChR agonist remains in the preparation throughout the storage period, enhancing platelet stability in storage and minimizing what is commonly referred to as platelet storage lesions (PSLs). By minimizing PSLs, the method 160 further increases platelet storage yield as it prevents platelet activation and thus aggregation during storage.

Although described in relation to a particular set of operations, in other embodiments, the method 160 may include more or fewer operations. For example, in some embodiments, no fluid is returned to the subject (166). In yet another scenario, in which prime platelets are to be returned to the subject, an incubation period may be added after operation 172 to incubate the platelet-rich mix (thus prime the platelets) and then return the primed platelets to the subject, in some cases along with all or some of the other blood components. In another example, an anticoagulant may be added prior to separation (e.g., as described in relation to operation 106 of FIG. 1A). Further, although described in relation to a particular series of operations, in further embodiments, certain operations of the method 160 may be performed in a different order and/or at least partially concurrently. For example, in some embodiments, the $Ca^{2+}$ and α7nAChR reagents are added (170, 172) prior to adding the liquid medium (168). In this manner, a smaller quantity of the $Ca^{2+}$ and α7nAChR reagents may need to be added. In illustration, after approximately ten seconds, the α7nAChR may have attached to receptors and enabled activation. At this point, the liquid medium (168) may be added without significant dilution of the effect of the $Ca^{2+}$ and α7nAChR reagents on the whole blood. Further, by timing the treatment of the whole blood prior to adding the liquid medium in this manner, a smaller volume of reagents will precipitate in the platelet-rich preparation. However, to enable the swift reaction of the reagents with the whole blood, it may be beneficial to incubate and agitate prior to adding the liquid medium. Other modifications to the method 160 are possible.

Figure 3A:
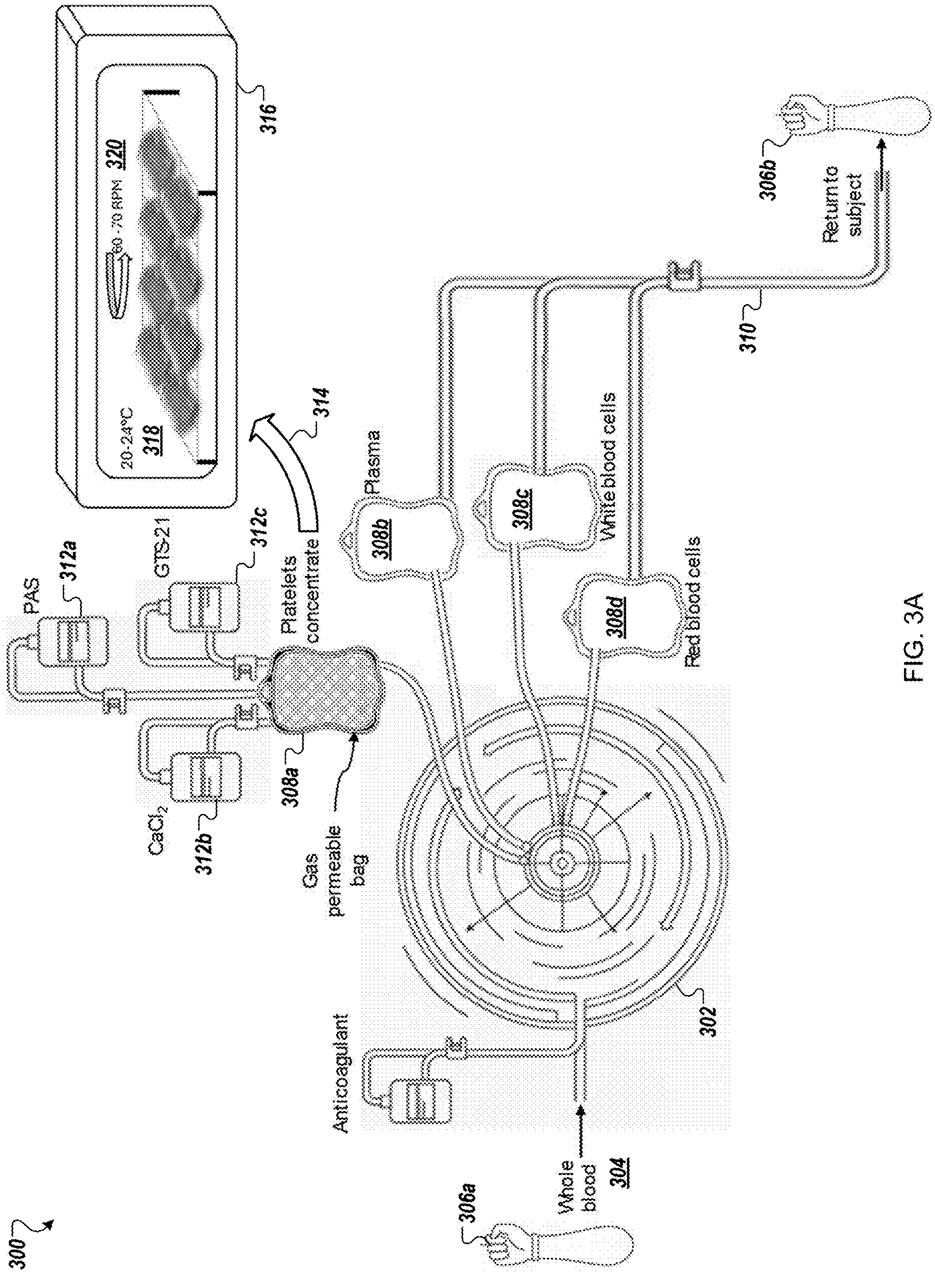
FIG. 3A is a flow diagram of an example process for producing platelets having enhanced coagulation capabilities.

Turning to FIG. 3A, a schematic diagram illustrates an example system 300 configured for ex-vivo platelet enhancement (aka platelet priming) using an apheresis device 302 is illustrated. The system 300 processes whole blood 304 drawn from a subject 306 through an apheresis centrifuge (shown as the central circular component). The apheresis device 302 separates the whole blood 304 into its constituent components 308, e.g., platelet concentrate 308*a*, plasma 308*b*, red blood cells 308*d*, and white blood cells 308*c*. The process illustrated within the system 300*k*, for example, may enable treatment of patients with coagulation deficiencies by periodically priming the patient's own blood. The patient, for example, may have hemophilia or other coagulation deficiency (e.g., vWD) and may be treated at least once per month using the process described in relation to the system 300. In other embodiments, the patient may be treated multiple times per month, such as every week or every other week. To maintain primed state, in some embodiments, the patient may continue to boost platelet priming between platelet treatments using neurostimulation, as described for example in U.S. Pat. No. 12,390,640 to Covalin et al. entitled "Electrical Stimulation Methods and Devices for Improving Blood Management" and incorporated by reference herein. The neurostimulation maintenance, for example, may be performed in some circumstances outside of a clinical setting (e.g., at home).

The separated components 308 flow into individual collection pathways. Any or all of the plasma 308*b*, red blood cells 308*d*, and white blood cells 308*c*, in some embodiments, are returned to the subject 306 as shown by a return pathway 310. In other embodiments, one or more of the plasma 308*b*, red blood cells 308*d*, and/or white blood cells 308*c* may be stored (not shown). The platelet concentrate 308*a* may be collected in a gas-permeable bag suitable for platelet storage as a blood component unit.

In some implementations, the system includes multiple reagent sources 312 connected to the apheresis device 302, shown as a set of reservoir bags. In other embodiments, the reagents may be stored in vials, rigid reservoirs, or another set of storage compartments. These reagents may include, in some examples, an anticoagulant to prevent premature coagulation during processing, a Platelet Additive Solution (PAS) 312*a* for maintaining platelet viability during storage, a source of $Ca^{2+}$ ions 312*b* (e.g., Calcium chloride ($CaCl_2$))), and a α7nAChR agonist 312*c* (e.g., GTS-21) for activating the α7nAChR pathway.

The reagents 312, in some implementations, are added to the platelet concentrate at the appropriate concentrations to achieve a final concentrations of around 1.5 mM $Ca^{2+}$ and around 10-100 μM GTS-21 (other concentrations may be used depending on the specific α7nAChR agonist used, such as those listed above in Table 3).

After reagent addition, in some embodiments, the platelet concentrate 308*a* in the gas-permeable bag is transferred 314 to a storage container 316. In other embodiments, the treated blood (e.g., all of components of 308*a-d*) with the primed platelets in it or the primed platelets-rich mix 308*a* by itself can be returned to the subject for autologous applications. In these autologous applications an extra step (not shown) to prime the platelets is added to the process (i.e., incubation by gentle agitation at room temperature of the platelet-rich mix for up to thirty minutes).

The storage device 316, in some implementations, functions as an incubator and an agitator. The storage device 316 includes a temperature-controlled chamber 318 configured to maintain platelets at 20-24° C., the standard temperature range for platelet storage. The storage container 316 further includes an agitation mechanism 320 configured to provide continuous gentle agitation, for example at approximately 60-70 RPM. This agitation prevents platelet settling and aggregation while promoting gas exchange through the gas-permeable storage bags. The gas-permeable bags, for example, allow oxygen and carbon dioxide exchange necessary for maintaining platelet metabolic activity and pH during storage. As illustrated, a collection of platelet preparations may be stored within gas-permeable bags in the chamber 318.

As previously noted, the storage device 316 serves a dual purpose in the context of the present invention. For storage applications, such as those described in relation to FIG. 1A and FIG. 1C, after the $Ca^{2+}$ and α7nAChR agonist are added to the platelet preparation, the preparation can be placed directly into this storage system. The storage conditions-room temperature (~20-25° C.) with gentle continuous agitation—provide the environment for α7nAChR activation and platelet priming to occur during the initial storage time (e.g., the first handful of minutes, such as under or about ten minutes or within ten to thirty minutes) after the platelet preparation enters storage. Therefore, no separate incubation device or dedicated incubation step prior to storage is required.

The α7nAChR agonist remains in the preparation throughout the storage period (1-14 days, typically 5 days), providing two benefits: the initial brief exposure primes the platelets for enhanced hemostatic function, and the continued presence of the agonist throughout storage reduces spontaneous platelet aggregation/activation, thereby improving storage quality and reducing the platelet storage lesion (PSL).

When the primed platelets or the primed platelets-rich mix is reintroduced via transfusion, either after storage or in an autologous methods, the α7nAChR agonist starts degrading due to its in-vivo half-life; thus restoring platelet activation back to normal. It is important to note that the reincorporation of fully functional platelets as the agonist is degraded happens gradually; however, even a small number of fully functional primed platelets is enough to produce a clinically meaningful effect. The inventors have produced evidence suggesting that a relatively small number of primed platelets is enough to show a clinical meaningful effect, as five minutes of auricular stimulation has shown to produce a clinically meaningful result. This phenomena is explained, for example, in U.S. Pat. No. 12,390,640 to Covalin et al. entitled "Electrical Stimulation Methods and Devices for Improving Blood Management," where neurostimulation promotes the release of ACh (a natural α7nAChR agonist) in close proximity to platelets in the spleen, thereby limiting bleeding from a wound by an approximate average of 50%.

Although described in relation to a particular set of operations, in other embodiments, the process performed using the system 300 may include more or fewer operations. For example, in certain embodiments, the process described in relation to FIG. 3A, instead of including separate reagents 312, may include a pre-mixed reagent compound (312*b*, 312*c*) or a premixed processing additive (including liquid medium 312*a*).

Figure 3B:
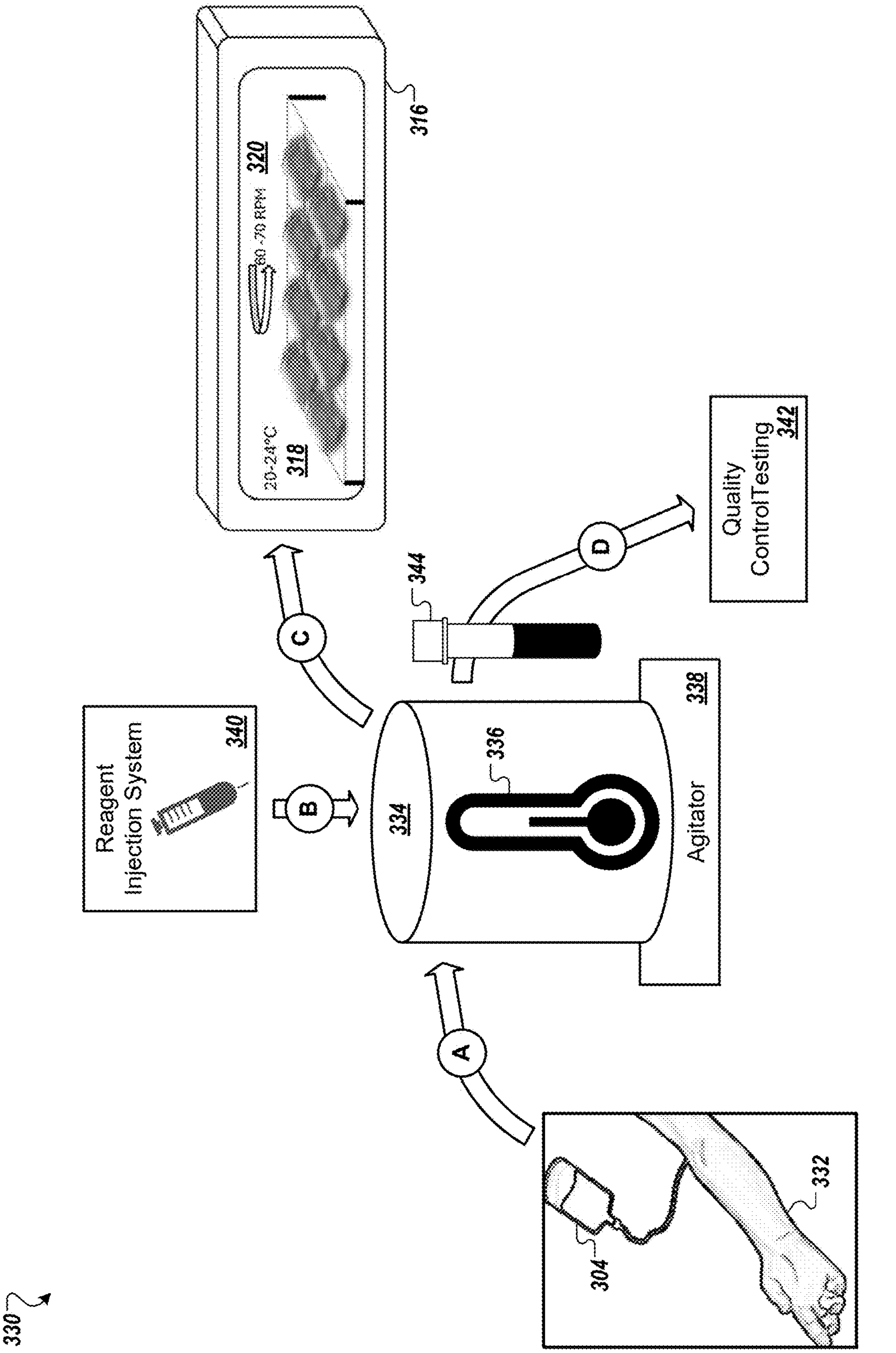
FIG. 3B is a flow diagram for an example process for producing whole blood having enhanced coagulation capabilities.

Turning to FIG. 3B, a flow diagram of an example process 330 for producing whole blood having enhanced coagulation capabilities is illustrated. The process 330, for example, may perform certain operations of the method 130 of FIG. 1B. Portions of the process 330 are similar to the process described in relation to the system 300 of FIG. 3A and/or may use the same or similar equipment to the process the process described in relation to the system 300 of FIG. 3A.

In some implementations, the process 330 begins with collecting whole blood 304 from a subject 332. As illustrated, the whole blood 304 is collected in a blood collection bag (e.g., a blood unit). However, the whole blood 304, in other embodiments, may be collected in one or more vials (e.g., a blood unit) or transferred directly to a processing chamber 334. The whole blood 304 may be collected, for example, as described in relation to operation 132 of FIG. 1B.

In some implementations, the whole blood 304 is deposited in a processing chamber 334. The processing chamber 334, for example, may be configured with thermal controls 336 for maintaining the whole blood 304 in physiological conditions (e.g., within a typical range of human body internal temperatures, such as a physiological temperature range of about 36-38° C.) as described, for example, in relation to operation 104 of FIG. 1A. In other embodiments, the processing chamber 334 is positioned in a thermally controlled environment (e.g., a device including the processing chamber 334 or a separate device holding the processing chamber 334).

The processing chamber 334, in some embodiments, includes an agitator 338 or is positioned upon or within the agitator 338. The agitator 338, for example, may be included in a same device that includes the processing chamber 334 or may be configured to accept or cooperate with the device that includes the processing chamber 334. The agitator 338 may be configured to gently agitate the whole blood 304 while the whole blood 304 is within the processing chamber 334. The agitator 338, for example, may agitate the whole blood 304 as described in relation to operation 112 of FIG. 1A.

In some embodiments, a reagent injection system 340 is configured to add at least a calcium rich reagent and a platelet transmembrane $Ca^{2+}$ channel agonist to the whole blood 304. In some embodiments, the reagent injection system 340 is included in same device as the processing chamber 334. In other embodiments, the reagent injection system 340 is a separate device in fluidic communication with the processing chamber 334. The reagent injection system 340, for example, may be in fluidic communication with one or more injection ports of the processing chamber 334 for introducing reagents.

The reagent injection system 340, in some embodiments, holds a premixed composition of reagents. In other embodiments, the reagent injection system 340 includes or is in fluidic communication with separate volumes (e.g., chambers, bladders, etc.) of each of two or more reagents. The reagents, in some examples, can include at least one of the calcium sources of Table 1 and at least one of the agonist sources of Table 2. The reagent injection system 340, further, may include at least one anticoagulant for introducing into the whole blood 304 in the processing chamber 334.

In some embodiments, the reagent injection system 340 is configured to controllably add two or more reagents to the processing chamber 334 in accordance with one or more parameters. Certain parameters (e.g., volume of the whole blood 304, weight of the whole blood 304, etc.), for example, may be measured by one or more sensors 334 of the processing chamber 334. In another example, certain parameters may include user-defined parameters, such as contents of each of one or more reagent sources within or in fluidic communication with the reagent injection system 340. For example, based at least in part upon a selected agonist source of two or more agonist sources (e.g., such as the agonist sources of Table 2) and/or a selected calcium source of one or more calcium sources (e.g., such as the calcium sources of Table 1), the reagent injection system 340 may be configured to automatically mix and/or inject reagents into the processing chamber 334. The reagent injection system 340, for example, may be programmed to determine reagent volumes based on preconfigured ratios, such as the example measurements indicated in Table 3. The agonists may be added, for example, in a manner similar to that described in relation to operations 140 and 142 of FIG. 1B.

The reagent injection system 340, in some embodiments, includes a user interface for controlling inclusion of reagents, identifying types of reagents, and/or confirming introduction of reagents. A display screen may be included on the reagent injection system 340 with buttons and/or a touch screen configured to receive user input. In another example, a computing device executing an application for controlling the reagent injection system 340 may be in wired or wireless communication with the reagent injection system 340.

In some implementations, the whole blood is agitated and incubated with the reagents in the processing chamber 334 for an incubation period. The incubation period may be timed, for example, by the reagent injection system 340 and/or the processing chamber 334. The incubation period may be selectable in part through user preferences.

In some implementations, upon completion of the incubation period (e.g., as described in relation to operation 146 of FIG. 1B), the whole blood is transferred to a storage device. The whole blood may be stored, for example, as one or more blood units, such as one or more gas-permeable bags and/or vials. The storage device may be the storage device 316 described in relation to FIG. 3A or another device configured to maintain the whole blood 304 in storage (e.g., in bags as illustrated in relation to storage device 316) within warm or cold storage conditions listed in Table 5 above.

In some implementations, to confirm the primed platelet content of the whole blood 304, quality control testing 342 is performed on a small sample 344 of the prepared whole blood. The quality control testing 342 may be configured to estimate a portion (e.g., percentage) of platelets primed within the whole blood content. Further, the quality control testing 342 may quantify residual quantities of one or more reagents within the whole blood sample 344. The quality control testing 342, in illustration, may include testing for one or more platelet activation markers, such as P-selectin.

Although described in relation to a particular set of operations, in other embodiments, the process 330 may include more or fewer operations. For example, to avoid destroying small quantities of whole blood product, quality control testing 342 may be foregone. Other modifications to the process 330 are possible.

Further, although described in relation to whole blood processing, in some embodiments, the system 300 of FIG. 3A includes the reagent injection system 340. The reagent injection system 340, for example, may be configured to controllably add liquid medium in addition to reagents.

Reference has been made to illustrations representing methods and systems according to implementations of this disclosure. Aspects thereof may be implemented by computer program instructions. These computer program instructions may be provided to a processor of a general-purpose computer, special purpose computer, or other programmable data processing apparatus and/or distributed processing systems having processing circuitry, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors. The virtual processors, for example, may be part of one or more physical computing systems such as a computer farm or a cloud drive.

Aspects of the present disclosure may be implemented by software logic, including machine readable instructions or commands for execution via processing circuitry. The software logic may also be referred to, in some examples, as machine readable code, software code, or programming instructions. The software logic, in certain embodiments, may be coded in runtime-executable commands and/or compiled as a machine-executable program or file. The software logic may be programmed in and/or compiled into a variety of coding languages or formats.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations (e.g., for different object schema dimensions). The hardware logic may be synthesized on a reprogrammable computing chip such as a field programmable gate array (FPGA) or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above.

The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in flash memory, random access memory (RAM), read-only memory (ROM), programmable ROM (PROM), erasable PROM (EPROM), electrically erasable PROM (EEPROM), dynamic random-access memory (DRAM), non-volatile random-access memory (NVRAM), static random-access memory (SRAM), hard disk or any other information processing device with which the computing device communicates, such as a server or computer. In another example, the memory may be incorporated into the processing circuitry as an on-chip memory unit. The processing circuitry and stored instructions may enable the computing device to perform, in some examples, certain control aspects of the method 100 of FIG. 1A, the method 130 of FIG. 1B, the method 160 of FIG. 1C, the process performed on the system 300 of FIG. 3A, and/or the process 330 of FIG. 3B.

These computer program instructions can direct a computing device or other programmable data processing apparatus to function in a particular manner, such that the instructions stored in the computer-readable medium produce an article of manufacture including instruction means which implement the function/operation specified in the illustrated process flows.

The computing device, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display.

Moreover, the present disclosure is not limited to the specific circuit elements described herein, nor is the present disclosure limited to the specific sizing and classification of these elements. For example, the skilled artisan will appreciate that the circuitry described herein may be adapted based on changes in battery sizing and chemistry or based on the requirements of the intended back-up load to be powered.

The functions and features described herein may also be executed by various distributed components of a system. For example, one or more processors may execute these system functions, where the processors are distributed across multiple components communicating in a network. The distributed components may include one or more client and server machines, which may share processing, in addition to various human interface and communication devices (e.g., display monitors, smart phones, tablets, personal digital assistants (PDAs), etc.). The network may be a private network, such as a LAN or WAN, or may be a public network, such as the Internet. Input to the system, in some examples, may be received via direct user input and/or received remotely either in real-time or as a batch process.

Although provided for context, in other implementations, methods and logic flows described herein may be performed on modules or hardware not identical to those described. Accordingly, other implementations are within the scope that may be claimed.

While certain embodiments have been described, these embodiments have been presented by way of example only and are not intended to limit the scope of the present disclosure. Indeed, the novel methods, apparatuses and systems described herein can be embodied in a variety of other forms; further, various omissions, substitutions and/or changes in the form of the methods, apparatuses and systems described herein can be made without departing from the spirit of the present disclosure. The accompanying claims and their equivalents are intended to cover such forms or modifications as would fall within the scope and spirit of the present disclosure.

What is claimed is:

1. A method for enhancing platelet function ex-vivo, the method comprising:

obtaining a volume of whole blood extracted from a subject;

treating at least a portion of the volume of whole blood with calcium ions and one or more reagents, each reagent configured to activate at least one transmembrane $Ca^{2+}$ channel of one or more transmembrane $Ca^{2+}$ channels, wherein the calcium ions and one or more reagents, in combination, are configured to cause a portion of platelets within the volume of whole blood to undergo enhancement via activation of the one or more transmembrane $Ca^{2+}$ channels, thereby producing a population of enhanced platelets within the volume of whole blood having increased $Ca^{2+}$ for enhanced coagulation capability, the at least one transmembrane $Ca^{2+}$ channel comprises a α7-Nicotinic Acetylcholine Receptor (α7-nAChR), and the one or more reagents comprises an α7-nAChR agonist; and after treating the at least the portion of the volume of whole blood, incubating the at least the portion of the volume of whole blood within a predetermined temperature range, and preparing the at least the portion of the volume of whole blood for storage and transferring to one or more storage compartments as one or more blood or blood component units, wherein a portion of platelets within the at least the portion of the whole blood, during the incubating, undergo the enhancement via activation of the one or more transmembrane $Ca^{2+}$ channels, thereby producing a population of enhanced platelets within the at least the portion of the volume of whole blood having increased $Ca^{2+}$ for enhanced coagulation capability.

2. The method of claim 1, wherein the predetermined temperature range spans from 20° C. to 38° C.

3. The method of claim 1, wherein the predetermined temperature range is a room temperature range.

4. The method of claim 1, wherein the predetermined temperature range is a physiological temperature range.

5. The method of claim 4, further comprising introducing the at least the portion of the volume of whole blood into a chamber configured to maintain the volume of whole blood at one or more temperatures within the physiological temperature range, wherein the at least the portion of the volume of whole blood is treated while in the chamber.

6. The method of claim 5, wherein incubating the at least the portion of the volume of whole blood comprises maintaining the at least the portion of the volume of whole blood in the chamber within the predetermined temperature range and under agitation.

7. The method of claim 1, wherein to incubate the at least the portion of the volume of whole blood comprises storing the one or more blood or blood component units in a storage chamber maintained within the predetermined temperature range.

8. The method of claim 1, wherein the one or more storage compartments are one or more gas-permeable storage bags.

9. The method of claim 1, wherein treating the at least the portion of the volume of whole blood prevents platelet aggregation during storage.

10. The method of claim 9, further comprising repeating the obtaining, the treating, and the incubating for a plurality of volumes of whole blood, thereby increasing platelet storage yield among the plurality of volumes of whole blood by preventing platelet aggregation and/or activation during storage.

11. The method of claim 1, wherein to incubate comprises incubating for at least five minutes.

12. The method of claim 1, wherein the at least the portion of the volume of whole blood is a volume of separated platelets in a liquid medium.

13. The method of claim 12, wherein a volume of the calcium ions added is determined based in part on a concentration of calcium included in the liquid medium.

14. The method of claim 12, further comprising:

separating the volume of separated platelets from the volume of whole blood; and adding the liquid medium to the volume of separated platelets to produce a platelet-rich mix;

wherein treating the at least the portion of the volume of whole blood comprises treating the volume of separated platelets.

15. The method of claim 14, wherein the liquid medium is added to the volume of separated platelets prior to treating the volume of separated platelets with the calcium ions and the one or more reagents.

16. The method of claim 14, further comprising adding, to the volume of whole blood, an anticoagulant prior to separating the volume of separated platelets from the volume of whole blood.

17. The method of claim 1, wherein obtaining the volume of whole blood comprises extracting the volume of whole blood using an apheresis machine.

18. The method of claim 1, wherein treating the at least the portion of the volume of whole blood comprises adding the calcium ions to the at least the portion of the volume of whole blood prior to adding the one or more reagents.

19. The method of claim 1, wherein:

the α7-nAChR agonist is GTS-21; and a volume of a 10 mM stock solution containing the α7-nAChR agonist is about 1.5 milliliters (mL) per 300 mL of the at least the portion of the volume of whole blood.

20. The method of claim 19, wherein the α7-nAChR agonist comprises at least one of GTS-21, 4-OH-GTS-21, PNU-282987, or ABT-107.

21. The method of claim 1, wherein the at least one transmembrane $Ca^{2+}$ channel further comprises at least one of a calcium-release activated calcium modulator 1 (CRACM1), a canonical transient receptor potential 6 (TRPC6), a purinergic receptor P2X, $Na^+/Ca^{2+}$ exchanger, or a plasma membrane $Ca^{2+}$ ATPases (PMCAs).

22. The method of claim 1, further comprising agitating the at least the portion of the volume of whole blood during the incubating.

23. The method of claim 22, wherein to agitate comprises agitating at 60 to 70 revolutions per minute (rpm).

24. The method of claim 1, wherein treating the at least the portion of the volume of whole blood with calcium ions comprises adding calcium chloride to obtain a working concentration in the at least the portion of the volume of whole blood within a range of 1.0-2.5 millimolar.

25. The method of claim 1, wherein:

the α7-nAChR agonist is GTS-21; and treating the at least the portion of the volume of whole blood with the one or more reagents comprises adding the GTS-21 to obtain a working concentration in the at least the portion of the volume of whole blood within a range of 40-60 micromolar.

* * * * *